United States Patent [19]

Konno et al.

[11] 4,254,056
[45] Mar. 3, 1981

[54] 2-AMINOMETHYL PHENOL DERIVATIVE AND PROCESS FOR PREPARING THEREOF

[75] Inventors: Mitoshi Konno, Kyoto; Hiroyuki Itoh, Suita; Takao Tokuhiro, Nagaokakyo; Katsumi Ohta; Masaki Hayashi, both of Takatsuki, all of Japan

[73] Assignee: Ono Pharmaceutical Co., Ltd., Osaka, Japan

[21] Appl. No.: 974,179

[22] Filed: Dec. 28, 1978

[30] Foreign Application Priority Data

Dec. 29, 1977 [JP] Japan ................... 53-158737

[51] Int. Cl.³ .................. C07C 87/20; C07C 91/30; A61K 27/00
[52] U.S. Cl. ................... 564/387; 424/330; 568/707
[58] Field of Search ............ 260/570.9, 570.8 R, 260/570.7; 568/707, 737, 734; 424/330

[56] References Cited

U.S. PATENT DOCUMENTS

| 3,072,716 | 8/1963 | Huebner | 260/501.1 |
| 3,504,031 | 3/1970 | Berdahl et al. | 568/734 |
| 3,642,785 | 2/1972 | Shen et al. | 568/734 |
| 3,794,734 | 2/1974 | Cragee et al. | 568/707 |
| 3,830,854 | 8/1974 | Degginger | 568/734 |
| 3,845,063 | 10/1974 | Balls | 568/731 |
| 4,076,843 | 2/1978 | Hauck et al. | 424/330 |
| 4,080,380 | 3/1978 | Zenitz | 260/570.5 |

OTHER PUBLICATIONS

Chemistry Letters, No. 1, 59–62, 1974, Claude Mareau et al.
Chemische Berichte, 93, 1774–1781, 1960, Horner et al.
Travaux de la Societe de Pharmacie de Montpellier, 24 No. 89–94, 1964, R. Granger et al.

Primary Examiner—Werren B. Lone
Attorney, Agent, or Firm—Sughrue, Rothwell, Mion, Zinn and Macpeak

[57] ABSTRACT

A 2-aminomethyl phenol derivative of the formula (I):

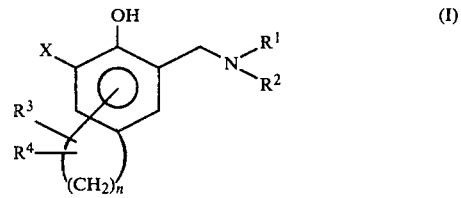

wherein X is a halogen atom; $R^1$, $R^2$, $R^3$ and $R^4$ which may be the same or different are each a hydrogen atom or a straight or branched chain alkyl group having 1 to 4 carbon atoms; n is 2, 3, 4 or 5 and a pharmaceutically acceptable acid addition salt thereof are disclosed. Also disclosed is a process for preparing such derivative or a pharmaceutically acceptable acid addition salt thereof.

15 Claims, No Drawings

2-AMINOMETHYL PHENOL DERIVATIVE AND PROCESS FOR PREPARING THEREOF

BACKGROUND OF THE INVENTION

1. Field of the Invention

This invention relates to a novel 2-aminomethyl phenol derivative and a process for preparing the same. More particularly, this invention relates to a 2-aminomethyl phenol derivative useful as a medicine, especially as an anti-inflammatory agent, of the formula (I):

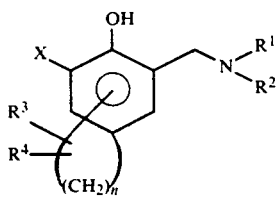

wherein X is a halogen atom; $R^1$, $R^2$, $R^3$ and $R^4$ which may be the same or different are each a hydrogen atom or a straight or branched chain alkyl group having 1 to 4 carbon atoms; n is 2,3,4 or 5 and pharmaceutically acceptable acid addition salts thereof.

It will be understood that the compound of this invention of the formula (I) can be more simply represented by the following two formulae:

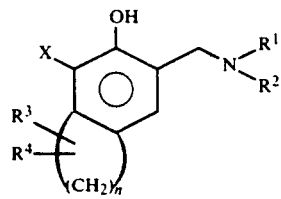

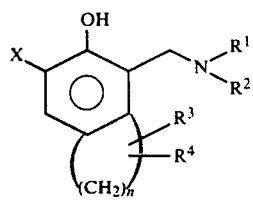

(wherein all symbols have the same meaning as defined above).

2. Description of the Prior Art

Conventional non-steroid acidic anti-inflammatory agents have been considered disadvantageous in that they have a side effect of developing a complication of gastric ulcer. As a result of studies on a novel anti-inflammatory agent free from the defect of the conventional anti-inflammatory agents, the compound of this invention which will be described in more detail hereinafter has been found. The compound of this invention has anti-inflammatory, analgesic, antipyretic, diuretic and hypotensive effects, and can be used for preventing and curing diseases caused by inflammation, edema, hypertension, etc.

SUMMARY OF THE INVENTION

Accordingly, a principal object of the present invention is to provide a non-steroid anti-inflammatory agent which is substantially free from the side effects which accompany conventional anti-inflammatory agents.

Another object of the present invention is to provide a compound having anti-inflammatory, analgesic, antipyretic, diuretic and hypotensive effects that can be used for preventing and curing deceases caused by inflammation, edema, hypertension, etc.

Still a further object of the present invention is to provide a compound having the above effects but free from the side effect of gastric ulcers.

Another object of the present invention is to provide a method for synthesizing such a compound.

These and other objects of the present invention are accomplished by the 2-aminomethylphenol compound of the present invention.

DETAILED DESCRIPTION OF THE INVENTION

The halogen atoms represented by X of the formula (I) are chlorine, bromine, fluorine and iodine atoms, and the iodine atom is preferred.

Examples of the $C_1$–$C_4$ alkyl groups represented by $R^1$, $R^2$, $R^3$ and $R^4$ of the formula (I) include a methyl group, an ethyl group, an n-propyl group, an isopropyl group, an n-butyl group, an isobutyl group, a sec-butyl group and a tert-butyl group. Preferably $R^1$, $R^2$, $R^3$ and $R^4$ are each a hydrogen atom or a methyl group.

Examples of preferred pharmaceutically acceptable acid addition salts of the compound of the formula (I) are inorganic acid salts such as hydrochloride, hydrobromide, hydroiodide, sulfate, phosphate, nitrate, etc., and organic acid salts such as acetate, lactate, tartrate, citrate, methanesulfonate, ethanesulfonate, benzenesulfonate, toluenesulfonate, isethionate, etc.

According to this invention, a 2-aminomethyl phenol derivative of the formula (I) wherein $R^2$ is a hydrogen atom and the other symbols are the same as defined above, or a compound of the formula (IV):

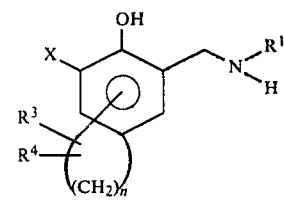

wherein the balance of the compound is as defined above is prepared by eliminating group $R^5$ of a compound of the formula (V):

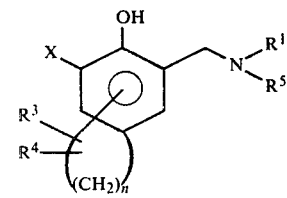

wherein $R^5$ is a formyl group, an alkylcarbonyl group having 2 to 5 carbon atoms or a haloalkylcarbonyl group having 2 to 5 carbon atoms or benzoyl group unsubstituted or substituted with at least one lower alkyl group having 1 to 3 carbon atoms, a hydroxyl group or halogen atom; and the other symbols are the same as defined above. Examples of such group $R^5$ are a formyl group, an acetyl group, a monochloroacetyl group, a propionyl group, a trichloroacetyl group, a benzoyl group, etc.

Elimination of group $R^5$ can be effected using an aqueous solution of an inorganic acid (1 to 10 equivalents) such as hydrochloric acid, hydrobromic acid, hydriodic acid, sulfuric acid, phosphoric acid and nitric acid in the presence of an inert organic solvent such as a lower alkanol such as methanol or ethanol or acetic acid, preferably in the presence of ethanol at a concentration of 5 to 20% (wt./vol) of the compound, at a temperature in the range from room temperature to the reflux temperature of the solvent used, preferably at the reflux temperature of the solvent used.

The product obtained may be purified either by recrystallization or by carbobenzoxydation which is followed by purification through recrystallization or chromatography which is then followed by elimination of the carbobenzoxy group. The product is obtained in the form of an acid addition salt of an inorganic acid. Free amine is obtained by neutralizing the acid addition salt in a conventional manner. An acid addition salt of inorganic acids other than the inorganic acid obtained or organic acids is obtained by adding an inorganic acid or organic acid to the free amine.

A compound of the formula (V) is obtained by reacting a compound of the formula (VI):

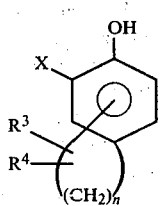
(VI)

wherein all symbols have the meaning defined above with 1 to 3 equivalents of a compound of the formula (VII):

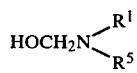
(VII)

wherein $R^1$ and $R^5$ are as defined above using a strong inorganic acid such as hydrochloric acid or sulfuric acid in the presence of a lower alkanol such as ethanol or an aliphatic acid such as acetic acid at a concentration of 5 to 20% (wt./vol) of compound (VI), normally at room temperature.

A compound of the formula (VI) is obtained by halogenating a compound of the formula (VIII):

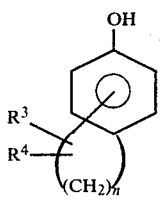
(VIII)

wherein all symbols mean the same as defined above. Halogenation is carried out either in the presence of an inert organic solvent such as chloroform, methylene chloride or benzene or acetic acid using a halogenating agent such as iodine monochloride, bromine, chlorine or sulfuryl chloride at a temperature in the range from room temperature to 100° C. or by reacting the compound of the formula (VIII) with an aqueous solution of iodine or a mixture of potassium iodide and iodine in the presence of an aliphatic amine such as primary or secondary amine, for example, ethylene diamine, morpholine, etc., using water, alcohol such as methanol or ethanol or water containing alcohol at a temperature ranging from room temperature to the reflux temperature of the solvent used.

A compound of the formula (V) may also be obtained from a compound of the formula (IX):

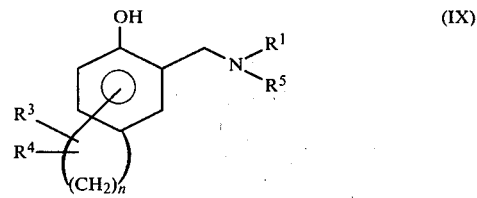
(IX)

wherein all symbols are as defined above under the same conditions for converting a compound of the formula (VIII) to a compound of the formula (VI).

A compound of the formula (IX) is obtained from a compound of the formula (VIII) using the conditions for converting a compound of the formula (VI) to a compound of the formula (V).

Further according to this invention, a compound of the formula (I) wherein $R^2$ is a straight or branched chain alkyl group having 1 to 4 carbon atoms and the other symbols are as defined above, or a compound of the formula (X):

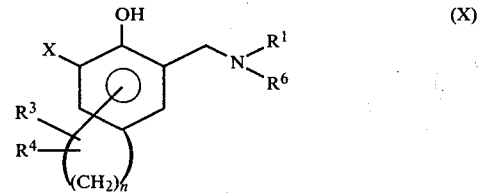
(X)

wherein $R^6$ is a straight or branched chain alkyl group having 1 to 4 carbon atoms, and the other symbols are the same as defined above is obtained by reacting a compound of the formula (VI) with 1 to 5 equivalents of a primary or secondary amine of the formula (XI):

(XI)

wherein $R^1$ and $R^6$ are each the same as defined above and 1 to 5 equivalents of formalin, or an aqueous solution of formaldehyde, in the presence or absence of a lower alkanol such as methanol or ethanol at a temperature ranging from 0° to 50° C., preferably at room temperature. Examples of suitable primary or secondary amines are methylamine, ethylamine, n-propylamine, isopropylamine, n-butylamine, sec-butylamine, dimethylamine, diethylamine, di-n-propylamine, di-n-butylamine, N-ethyl-n-butylamine, etc. Examples of preferred amines are dimethylamine and diethylamine. The product obtained can optionally be made into the form of an acid addition salt by a known method.

A compound of the formula (X) is also obtained from a compound of the formula (XII):

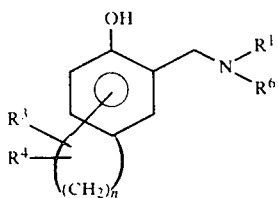

wherein all symbols are as defined above under the conditions for converting a compound of the formula (VIII) to a compound of the formula (VI).

A compound of the formula (XII) is obtained from a compound of the formula (VIII) under the conditions for converting a compound of the formula (VI) to a compound of the formula (X).

For conversion from a compound of the formula (VI) to a compound of the formula (V), from a compound of the formula (VIII) to a compound of the formula (IX), from a compound of the formula (VI) to a compound of the formula (X) or from a compound of the formula (VIII) to a compound of the formula (XII), or for a compound of the formula (VII), see *Organic Reactions,* 14, pp. 52–269, John Wiley & Sons, Inc., U.S.A.

The starting material of the formula (VIII) is either known or can be prepared by any of the methods described in the following publications:

(1) *Chemistry Letters,* No. 1, 59–62, 1974
(2) *Chemische Berichte,* 93, 1774–1781, 1960
(3) *Travaux de la Societe de Pharmacie de Montpellier,* 24, No. 1, 89–94, 1964.

Also, according to this invention, a compound of the formula (I) can be prepared from a compound of the formula (XIII) through the reaction taking the following course:

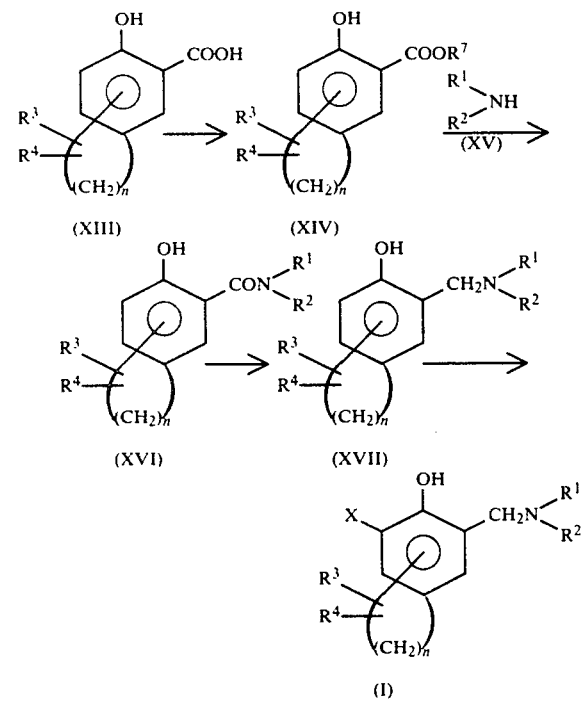

wherein $R^7$ is a lower alkyl group, and $R^1$, $R^2$, $R^3$, $R^4$ and n are each as defined above.

To be more specific, a compound of the formula (XIII) is esterified under ordinary esterification conditions which comprise, for example, maintaining a solution of the compound in an alkanol such as methanol, ethanol or n-propanol, preferably methanol or ethanol, for 1 to 10 hours at a temperature in the range from room temperature to the reflux temperature of the solvent in the presence of an acid such as hydrogen chloride gas, sulfuric acid or toluenesulfonic acid, or, alternatively, heating under reflux the compound as dissolved in benzene in the presence of the above alkanol and acid, while eliminating the resulting water. A compound of the formula (XIV) obtained is converted to a compound of the formula (XVI) by either reacting it with an amine of the formula (XV) in the presence of an inert organic solvent such as methanol, ethanol, benzene, toluene, tetrahydrofuran, dioxane, diethyl ether or under heat conditions at a temperature in the range from room temperature to the reflux temperature of the solvent or by maintaining the same reaction system in an autoclave at a temperature ranging from room temperature to 150° C. Examples of amines of the formula (XV) include ammonia and primary or secondary amines such as methylamine, ethylamine, n-propylamine, isopropylamine, n-butylamine, dimethylamine, diethylamine, di-n-propylamine, di-n-butylamine and N-methyl ethylamine. The compound of the formula (XVI) obtained is converted to a compound of the formula (XVII) by maintaining it in a solvent such as tetrahydrofuran, dioxane or 1,2-dimethoxyethane in the presence of 2 to 10 moles of a reducing agent such as lithium aluminum hydride, sodium borohydride, diborane, sodium aluminum dimethoxyethoxy hydride for 1 to 20 hours at a temperature in the range from room temperature to the reflux temperature of the solvent. A compound of the formula (I) is then obtained by halogenating the compound of the formula (XVII) under the conditions for converting a compound of the formula (IX) to a compound of the formula (V).

If a compound of the formula (XVII) is such that both $R^1$ and $R^2$ are a hydrogen atom or $R^1$ is a straight or branched chain alkyl group having 1 to 4 carbon atoms and $R^2$ is a hydrogen atom, the amino group may be protected before halogenation, followed by elimination of the protecting group, as illustrated by the following scheme:

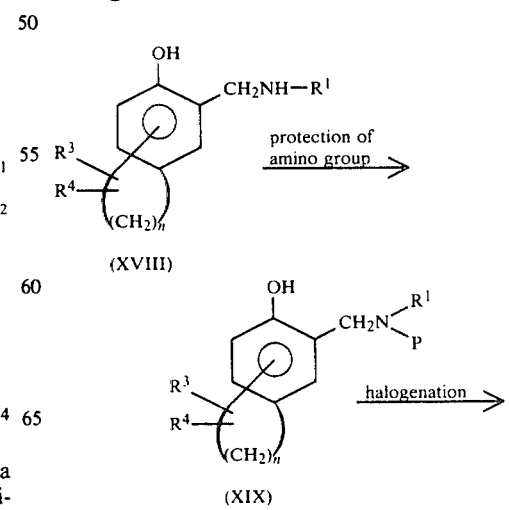

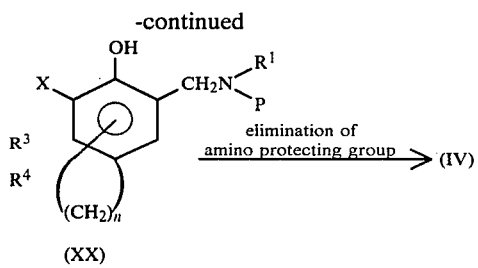

(XX)

wherein P is an amino protecting group, and $R^1$, $R^3$, $R^4$ and n are each the same as defined above.

The amino group of the compound of the formula (XVIII) may be protected by ordinary amino protecting groups, such as a carbobenzyloxy group, a tert-butoxycarbonyl group, an o-nitrophenylsulfenyl group, a formyl group, an acetyl group, a monochloroacetyl group or a trifluoroacetyl group. A preferred amino protecting group is a carbobenzyloxy group. These amino protecting groups can be introduced into the compound of the formula (XVIII) by a conventional method. A compound of the formula (XIX) obtained is converted to a compound of the formula (XX) under the same halogenation conditions described above, and then the latter compound has the amino protecting group eliminated to produce a compound of the formula (IV). The amino protecting group may be suitably eliminated by an ordinary method: the carbobenzyloxy group may be treated with a 30% solution of hydrobromic acid in acetic acid at 0° C. to room temperature whereas the tert-butoxycarbonyl group with a solution of trifluoroacetic acid or hydrochloric acid in acetic acid at room temperature.

The starting compound of the formula (XIII) is described in J. Org. Chem., 14, 366–374 (1949).

2-Aminomethyl phenol derivatives and pharmaceutically acceptable non-toxic salts thereof have anti-inflammatory, analgesic, antipyretic, diuretic and hypotensive effects, and so they can be advantageously used as an anti-inflammatory agent, analgesic, antipyretic, diuretic or urinating agent, and hypotensive agent. The following laboratory experiments demonstrate the effects of this compound.

(1) Wister male rats were orally administered with 1-iodo-3-aminomethyl-5,6,7,8-tetrahydro-2-naphthol hydrobromide, 1-aminomethyl-3-iodo-5,6,7,8-tetrahydro-2-naphthol hydrobromide, 4-iodo-6-aminomethyl-5-indanol hydrochloride and 1-iodo-3-aminomethyl-5,5-dimethyl-5,6,7,8-tetrahydro-2-naphthol hydrochloride, respectively, and the rats had carrageenan-induced edema in their paws inhibited.

One hour after oral administration with these compounds, the rats were subcutaneously injected with 0.1 m of 1% carrageenan suspension on the plantar surface of the right hind foot. The swelling was measured at the third hour of carrageenan injection. Anti-inflammatory effect of the compounds was determined as percentage inhibition of the swelling, taking the swelling in the control groups as 100%. The results of the test are shown in Table 1.

TABLE 1

Anti-Inflammatory Effect of the Compounds of this Invention on Carrageenan-Induced Edema in Rat Paws

| Compound | % Inhibition of Foot Edema | |
|---|---|---|
| | 10 mg/kg (%) | 30 mg/kg (%) |
| 1-Iodo-3-aminomethyl-5,6,7,8-tetrahydro-2-naphthol Hydrobromide | 68.8 | 69.6 |
| 1-Aminomethyl-3-iodo-5,6,7,8-tetrahydro-2-naphthol Hydrobromide | 55.6 | 68.8 |
| 4-Iodo-6-aminomethyl-5-indanol Hydrochloride | 41.1 | 55.8 |
| 1-Iodo-3-aminomethyl-5,5-dimethyl-5,6,7,8-tetrahydro-2-naphthol Hydrochloride | 44.1 | 66.3 |

As will be clear from the results shown in Table 2, the compound of this invention inhibits carageenan-induced edema well at low dosage levels.

(2) Upon oral administration with a dose of 3 mg/kg (body weight) of 1-iodo-3-aminomethyl-5,6,7,8-tetrahydro-2-naphthol hydrobromide, 1-aminomethyl-3-iodo-5,6,7,8-tetrahydro-2-naphthol hydrobromide, 4-iodo-6-aminomethyl-5-indanol hydrochloride, 1-iodo-3-(N,N-dimethylaminomethyl)-5,6,7,8-tetrahydro-2-naphthol hydrochloride and 1-methyl-4-iodo-6-aminomethyl-5-indanol hydrochloride, respectively, Wister male rats discharged increased amounts of urine.

About 16 hours before oral administration with 3 mg/kg of the compounds, the rats were starved, with only water available. The urinary volume during a 5 hour period after administration was compared with that of the control groups, taking the urinary volume of the latter as 100%. The results are shown in Table 2.

TABLE 2

Diuretic Effect of the Compounds of this Invention on Rats

| Compound | % Increase in Urinary Volume |
|---|---|
| 1-Iodo-3-aminomethyl-5,6,7,8-tetrahydro-2-naphthol Hydrobromide | 226 |
| 1-Aminomethyl-3-iodo-5,6,7,8-tetrahydro-2-naphthol Hydrobromide | 142 |
| 4-Iodo-6-aminomethyl-5-indanol Hydrochloride | 138 |
| 1-Iodo-3-(N,N-dimethylaminomethyl)-5,6,7,8-tetrahydro-2-naphthol Hydrochloride | 232 |
| 1-Methyl-4-iodo-6-aminomethyl-5-indanol Hydrochloride | 208 |

The following are examples of the 2-aminomethyl phenol derivative of the formula (I) according to this invention, however, the present invention should not be construed as being limited to these compounds.

3-iodo-5-aminomethyl-benzocyclobutene-4-ol; 3-aminomethyl-5-iodo-benzocyclobutene-4-ol; 3-iodo-5-(N-methylaminomethyl)benzocyclobutene-4-ol; 3-iodo-5-(N,N-dimethylaminomethyl)benzocyclobutene-4-ol; 3-(N-methylaminomethyl)-5-iodo-benzocyclobutene-4-ol; 3-(N,N-dimethylaminomethyl)-5-iodo-benzocyclobutene-4-ol; 4-iodo-6-aminomethyl-5-indanol; 4-aminomethyl-6-iodo-5-indanol; 4-iodo-6-(N-methylaminomethyl)-5-indanol; 4-iodo-6-(N,N-dimethylaminomethyl)-5-indanol; 4-(N-methylaminomethyl)-6-iodo-indanol; 4-(N,N-dimethylaminomethyl)-6-iodo-5-indanol; 1-methyl-4-iodo-6-aminomethyl-5-indanol; 1-methyl-4-aminomethyl-6-iodo-5-indanol; 1-methyl-4-iodo-6-(N-methylaminomethyl)-5-indanol; 1-methyl-4-iodo-6-(N,N-dimethylaminomethyl)-5- indanol; 1-methyl-4-(N-methylaminomethyl)-6-iodo-5-indanol; 1-methyl-4-(N,N-dimethylaminomethyl)-6-iodo-5-indanol; 1-iodo-3-aminomethyl-5,6,7,8-tetrahydro-2-naphthol; 1-aminomethyl-3-iodo-5,6,7,8-tetrahydro-2-naphthol; 1-iodo-3-(N-methylaminomethyl)-5,6,7,8-tetrahydro-2-naphthol; 1-iodo-3-(N,N-dimethylaminomethyl)-5,6,7,8-tetrahydro-2-naphthol; 1-(N-methylaminomethyl)-3-iodo-5,6,7,8-tetrahydro-2-naphthol, 1-(N,N-dimethylaminomethyl)-3-iodo-5,6,7,8-tetrahydro-2-naphthol; 1-iodo-3-aminomethyl-5-methyl-5,6,7,8-tetrahydro-2-naphthol; 1-aminomethyl-3-iodo-5-methyl-5,6,7,8-tetrahydro-2-naphthol; 1-iodo-3-(N-methylaminomethyl)-5-methyl-5,6,7,8-tetrahydro-2-naphthol; 1-iodo-3-(N,N-dimethylaminomethyl)5-methyl-5,6,7,8-tetrahydro-2-naphthol 1-(N-methylaminomethyl)-3-iodo-5-methyl-5,6,7,8-tetrahydro-2-naphthol 1-(N,N-dimethylaminomethyl)-3-iodo-5-methyl-5,6,7,8-tetrahydro-2-naphthol; 1-iodo-3-aminomethyl-8-methyl-5,6,7,8-tetrahydro-2-naphthol; 1-aminomethyl-3-iodo-8-methyl-5,6,7,8-tetrahydro-2-naphthol; 1-iodo-3-(N-methylaminomethyl)-8-methyl-5,6,7,8-tetrahydro-2-naphthol; 1-iodo-3-(N,N-dimethylaminomethyl)-8-methyl-5,6,7,8-tetrahydro-2-naphthol; 1-(N-methylaminomethyl)-3-iodo-8-methyl-5,6,7,8-tetrahydro-2-naphthol; 1-(N,N-dimethylaminomethyl)-3-iodo-8-methyl-5,6,7,8-tetrahydro-2-naphthol; 1-iodo-3-aminomethyl-5,5-dimethyl-5,6,7,8-tetrahydro-2-naphthol; 1-aminomethyl-3-iodo-5,5-dimethyl-5,6,7,8-tetrahydro-2-naphthol; 1-iodo-3-(N-methylaminomethyl)-5,5-dimethyl-5,6,7,8-tetrahydro-2-naphthol; 1-iodo-(N,N-dimethylaminomethyl)-5,5-dimethyl-5,6,7,8-tetrahydro-2-naphthol, 1-(N-methylaminomethyl)-3-iodo-5,5-dimethyl-5,6,7,8-tetrahydro-2-naphthol; 1-(N,N-dimethylaminomethyl)-3-iodo-5,5-dimethyl-5,6,7,8-tetrahydro-2-naphthol; 1-iodo-3-aminomethyl-6,7,8,9-tetrahydro-5H-benzocycloheptene-2-ol; 1-aminomethyl-3-iodo-6,7,8,9-tetrahydro-5H-benzocycloheptene-2-ol; 1-iodo-3-(N-methylaminomethyl)-6,7,8,9-tetrahydro-5H-benzocycloheptene-2-ol; 1-iodo-3-(N,N-dimethylaminomethyl)-6,7,8,9-tetrahydro-5H-benzocycloheptene-2-ol; 1-(N-methylaminomethyl)-3-iodo-6,7,8,9-tetrahydro-5H-benzocycloheptene-2-ol; 1-(N,N-dimethylaminomethyl)-3-iodo-6,7,8,9-tetrahydro-5H-benzocycloheptene-2-ol; 1-iodo-3-aminomethyl-5,5-dimethyl-6,7,8,9-tetrahydro-5H-benzocycloheptene-2-ol; 1-aminomethyl-3-iodo-5,5-dimethyl-6,7,8,9-tetrahydro-5H-benzocycloheptene-2-ol; 1-iodo-3-(N-methylaminomethyl)-5,5-dimethyl-6,7,8,9-tetrahydro-5H-benzocycloheptene-2-ol; 1-iodo-3-(N,N-dimethylaminomethyl)-5,5-dimethyl-6,7,8,9-tetrahydro-5H-benzocycloheptene-2-ol; 1-(N-methylaminomethyl)-3-iodo-5,5-dimethyl-6,7,8,9-tetrahydro-5H-benzocycloheptene-2-ol; and 1-(N,N-dimethylaminomethyl)-3-iodo-5,5-dimethyl-6,7,8,9-tetrahydro-5H-benzocycloheptene-2-ol.

Both oral and parenteral administrations are effective for curing and preventing diseases due to inflammation, edema and hypertension. A dose of 5 to 200 mg may desirably be administered once a day or more frequently. But exact dosages should be determined by the age, weight and condition of a patient as well as by the route and frequency of administration.

Solid preparations for oral administration include a tablet, pill, powder and granule, which has one or more active ingredients mixed with at least one inert diluent, such as half-digested starch, potato starch, alginic acid, mannite or lactose. The preparation may contain an additive other than the diluent, for example, a lubricant such as magnesium stearate, according to the conventional manner. Liquid preparations for oral administration include a pharmaceutically acceptable emulsion, solution, suspension, syrup or elixir containing a commonly employed inert diluent, for example, water or liquid paraffin. The preparation contains additives other than the inert diluent such as a wettener, suspension aid, sweetener, flavoring, aromatizer or antiseptic. Preparations for oral administration also include a capsule made of gelatin and other digestable substances containing one or more active ingredients and optionally a diluent or excipient.

Preparations for parenteral administration include a sterile aqueous or non-aqueous solution, suspension or emulsion. In making non-aqueous solutions or suspensions, propylene glycol, polyethylene glycol and vegetabl oils such as olive oil, and an injectable organic acid ester such as ethyl oleate may be used. Such preparations may contain such additives as antiseptic, wettener, emulsifier and dispersant, which can be sterilized by, for example, filtration through a bacteria capturing filter, compounding of a bactericide or irradiation with ultraviolet (radioactive) rays. Alternatively, a sterile solid preparation is first made and then dissolved in a sterile injectable solvent immediately before use.

This invention is now described in greater detail by reference to the following examples, which are given for illustrative purpose only and by no means limit the scope of this invention. In the examples, "TLC", "IR", "NMR" and "MS" mean "thin layer chromatography", "infrared absorption spectrum", "nuclear magnetic resonance spectrum" and "mass spectrum", respectively. The proportions of solvents of which a developing agent used for TLC is made are by volume.

EXAMPLE 1

1-Iodo-5,6,7,8-tetrahydro-2-naphthol and
3-Iodo-5,6,7,8-tetrahydro-2-naphthol

A 4.45 g solution of 5,6,7,8-tetrahydro-2-naphthol was dissolved in 25 ml of glacial acetic acid, mixed with 5.85 g of iodine monochloride and heated under reflux at 100° C. for 2 hours. After reaction, the reaction mixture was poured onto 100 ml of ice water and extracted with ethyl acetate. The extract was washed sequentially with an aqueous solution of sodium thiosulfate (hypo), water and saturated aqueous NaCl solution, dried with anhydrous magnesium sulfate, and concentrated under vacuum. The residue was purified by column chromatography on silica gel using an eluting agent comprising a mixture (1:2) of methylene chloride and cyclohexane to provide white crystals each comprising 2.11 g of 1-iodo-5,6,7,8-tetrahydro-2-naphthol and 2.84 g of 3-iodo-5,6,7,8-tetrahydro-2-naphthol having the following physical properties.

1-Iodo-5,6,7,8-tetrahydro-2-naphthol

Melting Point: 89°–90° C.

TLC (on a developer of methylene chloride): Rf=0.60.

IR (KBr tablet method): $\nu$=3300, 2920, 2850, 1600, 1565, 1480, 1440, 1410, 1350, 1280, 1260, 1170, 1120, 1070, 1000, 945, 930, 895, 870, 830, 800, 770, 730, 580, 540 cm$^{-1}$.

NMR (CDCl$_3$ solution): $\delta$=6.90 (1H, d, J=8.0 Hz), 6.70 (1H, d, J=8.0 Hz), 5.30 (1H, s), 3.0–2.2 (4H, m), 2.2–1.4 (4H, m).

3-Iodo-5,6,7,8-tetrahydro-2-naphthol

Melting Point: 70° C.

TLC (on a developer of methylene chloride); Rf=0.55.

IR (KBr tablet method): $\nu$=3220, 2920, 2850, 1770, 1740, 1595, 1500, 1450, 1410, 1370, 1350, 1330, 1310, 1275, 1235, 1185, 1145, 1000, 945, 935, 910, 850, 815, 745, 730, 630, 605, 550 cm$^{-1}$.

NMR (CDCl$_3$ solution): $\delta$=7.23 (1H, s), 6.60 (1H, s), 5.00 (1H, s), 3.0–2.4 (4H, m), 2.0–1.5 (4H, m).

EXAMPLE 2

1-Iodo-3-(N-chloroacetylaminomethyl)-5,6,7,8-tetrahydro-2-naphthol 1.26 g of 1-iodo-5,6,7,8-tetrahydro-2-naphthol as prepared in Example 1 was dissolved in 10 ml of a mixture (10:1) of glacial acetic acid and concentrated sulfuric acid, and mixed with 0.86 g of N-hydroxymethylchloroacetamide at 20° C. with stirring that continued for 10 minutes at the same temperature. The reaction mixture was then poured onto 50 ml of ice water and extracted with ethyl acetate. The extract was sequentially washed with water and saturated aqueous NaCl solution, dried with anhydrous magnesium sulfate and concentrated under vacuum. The residue was purified by column chromatography on silica gel using methylene chloride as an eluting agent, giving 1.12 g of a white crystal of the title compound having the following physical properties.

Melting Point: 133°–143° C.

TLC (methylene chloride as a developing agent); Rf=0.30.

IR (KBr tablet method): $\nu$=3320, 2920, 2850, 1620, 1550, 1450, 1430, 1410, 1370, 1340, 1290, 1260, 1240, 1180, 1160, 1100, 1020, 910, 830, 780, 750, 620, 595 cm$^{-1}$.

NMR (CDCl$_3$ solution); $\delta$=7.53 (1H, s), 7.5–6.9 (1H, m), 6.73 (1H, s), 4.37 (2H, d, J=6.0 Hz), 4.00 (2H, s), 3.0–2.4 (4H, m), 2.1–1.4 (4H, m).

EXAMPLE 3

1-Iodo-3-aminomethyl-5,6,7,8-tetrahydro-2-naphthol Hydrochloride

A solution of 1.08 g of N-chloroacetylamino compound (prepared in Example 2) in 10 ml of ethanol was mixed with 2 ml of concentrated hydrochloric acid and heated under reflux for 5 hours. The reaction mixture was concentrated under vacuum, and the residue was recrystallized from a solvent comprising a mixture of methanol and diethyl ether, giving 680 mg of a white crystal of the title compound having the following physical properties.

Melting Point: decomposed at a temperature higher than 200° C.

TLC (on a developer consisting of n-butanol/glacial acetic acid/water at 25:2:3): Rf=0.90.

IR (KBr table method): $\nu$=3000, 2930, 1580, 1460, 1430, 1380, 1320, 1260, 1230, 1140, 1120, 920, 860, 820, 780, 740 cm$^{-1}$.

NMR (dimethylsulfoxide-d$_6$ solution): $\delta$=9.6 (1H, broad s), 8.15 (3H, broad s), 7.1–6.4 (1H, m), 4.2–3.6 (2H, m), 2.8–2.3 (4H, m), 2.0–1.4 (4H, m).

EXAMPLE 4

1-Iodo-3-(N-carbobenzoxyaminomethyl)-5,6,7,8-tetrahydro-2-naphthol

A solution of 610 mg of amine hydrochloride (prepared in Example 3) in 4 ml of warm water was mixed with 4.0 ml of 1 N aqueous sodium hydroxide solution, further mixed with 400 mg of carbobenzoxychloride under stirring at room temperature, and the mixture was left standing for 10 minutes at room temperature. The reaction mixture was acidified with 1 N hydrochloric acid and extracted with ethyl acetate. The extract was sequentially washed with water and saturated aqueous NaCl solution, dried with anhydrous magnesium sulfate and concentrated under vacuum. The residue was purified by column chromatography on silica gel using methylene chloride as an eluting agent, giving 473 mg of a white crystal of the title compound having the following physical properties.

TLC (on a developer of methylene chloride); Rf=0.40.

IR (KBr tablet method): $\nu$=3300, 3050, 2920, 1760, 1670, 1610, 1545, 1455, 1380, 1360, 1290, 1250, 1180, 1140, 1090, 1030, 990, 920, 880, 825, 780, 735, 695, 580 cm$^{-1}$.

NMR (CDCl$_3$ solution): $\delta$=7.20 (6H, s), 6.73 (1H, s), 5.40 (1H, broad s), 5.00 (2H, s), 4.23 (2H, d, J=6.0 Hz), 2.9–2.4 (4H, m), 2.0–1.4 (4H, m).

EXAMPLE 5

1-Iodo-3-aminomethyl-5,6,7,8-tetrahydro-2-naphthol Hydrobromide

A mixture of 470 mg of the N-carbobenzoxyaminomethyl compound prepared in Example 4 and 1.0 g of 30% solution of hydrogen bromide in acetic acid was left standing at room temperature under occasional stirring until no more gas developed. To the reaction mixture was added 30 ml of diethyl ether, the precipitating solid was filtered off and washed with diethyl ether followed by drying. The resulting solid was recrystallized from a mixture of methanol and diethyl ether, giving 226 mg of a white crystal of the title compound having the following physical properties.

Melting Point: 204°–206° C.

TLC (on a developer consisting of n-butanol/glacial acetic acid/water at 5:2:3): Rf=0.70.

IR (KBr tablet method): $\nu$=3400, 3150–3000, 2930, 1600–1560, 1470, 1410, 1380, 1320, 1240–1210, 1180–1160, 1120, 780 cm$^{-1}$.

NMR (dimethylsulfoxide-d$_6$ solution): $\delta$=10.0–8.5 (1H, broad s), 8.5–7.5 (1H, broad s), 7.5–6.5 (1H, m), 4.03 (2H, broad s), 2.9–2.3 (4H, m), 2.0–1.4 (4H, m).

MS: m/e=303, 286, 177, 160, 159, 132, 131, 117, 115, 104, 91, 82, 80, 77.

EXAMPLE 6

1-(N-Chloroacetylaminomethyl)-3-iodo-5,6,7,8-tetrahydro-2-naphthol

The 3-iodo-5,6,7,8-tetrahydro-2-naphthol (prepared in Example 1) was treated by the procedure of Example 2, giving a white crystal of the title compound (yield of 45%) having the following physical properties.

Melting Point: 119°–125° C.

TLC (on a developing agent of methylene chloride): Rf=0.30.

IR (KBr tablet method): $\nu = 3370, 2930, 2860, 1630, 1550, 1455, 1415, 1340, 1260, 1235, 1190, 1160, 780, 760$ and $590 \text{ cm}^{-1}$.

NMR (CDCl$_3$ solution): $\delta = 7.93$ (1H, s), 7.5–6.9 (1H, broad s), 7.35 (1H, s), 4.47 (2H, d, J=6.0 Hz), 4.00 (2H, s), 3.0–2.5 (4H, m), 2.2–1.4 (4H, m).

EXAMPLE 7

1-Aminomethyl-3-iodo-5,6,7,8-tetrahydro-2-naphthol Hydrochloride

The N-chloroacetylaminomethyl compound (prepared in Example 6) was treated by the procedure of Example 3, giving 69% yield of a white crystal of the title compound having the following physical properties.

Melting Point: decomposed at a temperature higher than 180° C.

TLC (on a developer comprising n-butanol/glacial acetic acid/water at 5:2:3): Rf=0.90.

IR (KBr tablet method): $\nu = 3350, 2940, 1600, 1570, 1460, 1430, 1380, 1320, 1295, 1280, 1260, 1240, 1220, 1185, 1120, 1100, 950, 870, 855, 760, 740 \text{ cm}^{-1}$.

NMR (dimethylsulfoxide-d$_6$ solution): $\delta = 9.10$ (1H, broad s), 8.20 (3H, broad s), 7.40 (1H, s), 4.00 (2H, broad s), 2.0–2.4 (4H, m), 2.0–1.5 (4H, m).

EXAMPLE 8

1-(N-Carbobenzoxyaminomethyl)-3-iodo-5,6,7,8-tetrahydro-2-naphthol

The amine hydrochloride (prepared in Example 7) was treated by the procedure of Example 4, giving 59% yield of a white crystal of the title compound having the following physical properties.

TLC (on a developer of methylene chloride): Rf=0.50.

IR (KBr tablet method): $\nu = 3300, 3050, 2920, 1760, 1670, 1580, 1540, 1460, 1415, 1380, 1360, 1340, 1280, 1240, 1195, 1165, 1135, 1090, 1070, 1030, 975, 960, 915, 870, 830, 780, 760, 700, 620, 590, 580, 540, 460 \text{ cm}^{-1}$.

NMR (CDCl$_3$ solution): $\delta = 7.93$ (1H, broad s), 7.30 (1H, s), 7.20 (5H, s), 5.45 (1H, broad s), 5.00 (2H, s), 4.30 (2H, d, J=6.0 Hz), 2.8–2.4 (4H, m), 2.0–1.5 (4H, m).

EXAMPLE 9

1-Aminomethyl-3-iodo-5,6,7,8-tetrahydro-2-naphthol Hydrobromide

The N-carbobenzoxyaminomethyl compound (prepared in Example 8) was treated by the procedure of Example 5, giving 70% yield of a white crystal of the title compound having the following physical properties.

Melting Point: 215°–217° C.

TLC (on a developing agent comprising n-butanol/glacial acetic acid/water at 5:2:3): Rf=0.70.

IR (KBr tablet method): $\nu = 3360, 3050, 2940, 1600, 1560, 1465, 1455, 1435, 1405, 1375, 1320, 1300, 1280, 1260, 1245, 1190, 1110, 1100, 950, 895, 870, 855, 760, 735, 570 \text{ cm}^{-1}$.

NMR (dimethylsulfoxide-d$_6$ solution): $\delta = 7.51$ (1H, s), 4.04 (2H, broad s), 2.9–2.4 (4H, m), 2.0–1.4 (4H, m).

MS: m/e = 303, 286, 159, 130, 115, 103, 91, 82, 80, 77.

EXAMPLE 10

4-Iodo-5-indanol

The procedure of Example 1 was repeated to treat 5-indanol, giving 46% yield of a colorless transparent oily substance of the title compound having the following physical properties.

TLC (on a developer comprising methylene chloride/cyclohexane at 1:1)=Rf=0.40.

IR (film method): $\nu = 3470, 2950, 2850, 1750, 1600, 1570, 1480, 1460, 1440, 1375, 1335, 1280, 1240, 1230, 1190, 1100, 1020, 960, 910, 870, 815 \text{ cm}^{-1}$.

NMR (CDCl$_3$ solution): $\delta = 7.5$–6.6 (3H, m), 5.26 (1H, s), 3.3–1.8 (6H, m).

EXAMPLE 11

4-Iodo-6-(N-chloroacetylaminomethyl)-5-indanol

The procedure of Example 2 was repeated to treat the iodine compound from Example 10, giving 66% yield of a white crystal of the title compound having the following physical properties.

TLC (on a developing agent comprising methylene chloride/cyclohexane at 1:1): Rf=0.10.

IR (KBr tablet method): $\nu = 3300, 3100, 2920, 1630, 1560, 1450, 1430, 1410, 1370, 1290, 1250, 1230, 1190, 1150, 1070, 1010, 930, 860, 795, 720, 630, 580, 540, 440 \text{ cm}^{-1}$.

NMR (CDCl$_3$ solution): $\delta = 7.98$ (1H, broad s), 7.60–7.30 (1H, broad s), 6.95 (1H, s), 4.44 (2H, d, J=6.5 Hz), 4.05 (2H, s), 3.15–2.70 (4H, m), 2.30–1.85 (2H, m).

EXAMPLE 12

4-Iodo-6-aminomethyl-5-indanol Hydrochloride

The N-chloroacetylaminomethyl compound (prepared in Example 11) was treated by the procedure of Example 3, giving 65% yield of a white crystal of the title compound having the following physical properties.

Melting Point: decomposed at 212°–217° C.

TLC (on a developer comprising n-butanol/glacial acetic acid/water at 5:2:3): Rf=0.73.

IR (KBr tablet method): $\nu = 3200, 2950, 1605, 1570, 1480, 1450, 1430, 1375, 1280, 1140, 880 \text{ cm}^{-1}$.

NMR (dimethylsulfoxide-d$_6$ solution): $\delta = 7.1$ (1H, s), 3.9 (2H, s), 3.2–2.5 (4H, m), 2.3–1.7 (2H, m).

EXAMPLE 13

6-(N-Chloroacetylaminomethyl)-5-indanol

The procedure of Example 2 was repeated using 5-indanol instead of the 1-iodo compound prepared in Example 1, giving 32% yield of a white crystal of the title compound having the following physical properties.

TLC (on a developer of methylene chloride): Rf=0.20.

NMR (CDCl$_3$+dimethylsulfoxide-d$_6$ solution): $\delta = 9.2$ (1H, broad s), 8.3 (1H, broad s), 7.20 (1H, s), 6.90 (1H, s), 4.45 (2H, d, J=6.0 Hz), 4.15 (2H, s), 3.2–2.5 (4H, m), 2.5–1.7 (2H, m).

EXAMPLE 14

4-Iodo-6-(N-chloroacetylaminomethyl)-5-indanol

The N-chloroacetylaminomethyl compound (prepared in Example 13) was iodated by the procedure of Example 1, giving 31% yield of the title compound having the same physical properties as those of the compound prepared in Example 11.

EXAMPLE 15

1-Iodo-3-(N-acetyl-N-methyl)aminomethyl-5,6,7,8-tetrahydro-2-naphthol

The 1-iodo-5,6,7,8-tetrahydro-2-naphthol (prepared in Example 1) was treated by repeating the procedure of Example 2 except that N-hydroxymethylchloroacetamide was replaced by N-methyl-N-hydroxymethylacetamide, giving 50% yield of a white crystal of the title compound having the following physical properties.

Melting Point: 184°–185° C.

TLC (on a developer of methylene chloride): Rf=0.13.

IR (KBr tablet method): $\nu = 1605$ cm$^{-1}$.

NMR (CDCl$_3$ solution): $\delta = 6.70$ (1H, s), 4.35 (2H, s), 3.00 (3H, s), 2.90–2.35 (4H, m), 2.05 (3H, s), 2.00–1.45 (4H, m).

EXAMPLE 16

1-Iodo-3-(N-methylaminomethyl)-5,6,7,8-tetrahydro-2-naphthol Hydrochloride

The procedure of Example 3 was repeated to treat the (N-acetyl-N-methyl)aminomethyl compound (prepared in Example 15), giving 85% yield of a white crystal of the title compound having the following physical properties.

TLC (on a developer comprising ethyl acetate/acetic acid/water at 3:1:1): Rf=0.58.

IR (KBr tablet method): $\nu = 2940, 2700-2250, 1610, 1465, 1315$ cm$^{-1}$.

NMR (CDCl$_3$ solution): $\delta = 9.35-8.00$ (1H, broad s), 7.00 (1H, broad s), 7.1–6.15 (1H, m), 4.5–3.6 (2H, m), 3.3–2.0 (7H, m), 2.0–1.3 (4H, m).

EXAMPLE 17

1-Iodo-3-(N,N-dimethylaminomethyl)-5,6,7,8-tetrahydro-2-naphthol

To a mixture of a solution of 513.1 mg of 1-iodo-5,6,7,8-tetrahydro-2-naphthol (prepared in Example 1) in 1 ml of methanol and 0.2104 ml of 40% dimethylamine aqueous solution was added 0.1515 ml of 37% formalin at 0° to 5° C., and the resulting solution was stirred at room temperature for 2 hours. The reaction mixture was concentrated under vacuum, and the resulting residue was purified by column chromatography on silica gel using an eluting agent comprising a mixture of ethyl acetate and cyclohexane (1:4), giving 230 mg of a pale brown oily product of the title compound having the following physical properties.

TLC (on a developing agent comprising ethyl acetate and cyclohexane at 1:1) Rf=0.40.

IR (film method): $\nu = 2936, 2890, 2870, 2840, 2798, 1615, 1439, 1300, 1259, 1885$ (1085?), 1018, 780, 738 cm$^{-1}$.

NMR (CDCl$_3$ solution): $\delta = 8.50$ (1H, broad s), 6.57 (1H, s), 3.53 (2H, s), 2.67 (4H, m), 2.30 (6H, s), 1.72 (4H, m).

MS: m/e=331, 286, 159.

EXAMPLE 18

1-Iodo-3-(N,N-dimethylaminomethyl)-5,6,7,8-tetrahydro-2-naphthol Hydrochloride

A solution of 230 mg of the N,N-dimethylamino compound (as prepared in Example 17) in 20 ml of methanol was mixed with 0.2 ml of concentrated hydrochloric acid under stirring. The solution mixture was filtered on activated carbon, and the filtrate concentrated under vacuum. The residue was recrystallized from a mixture of methanol and diethyl ether, giving 156 mg of a white crystal of the title compound having the following physical properties.

Melting Point: 30°–33° C.

TLC (on a developing agent comprising ethyl acetate and cyclohexane 1:1): Rf=0.50.

IR (KBr tablet method): $\nu = 3300, 2940, 2855, 2830, 2700, 1630, 1460, 1415, 1310, 1280, 1160, 1095, 780$ cm$^{-1}$.

NMR (CDCl$_3$+D$_2$O solution): $\delta = 7.09$ (1H, broad s), 4.16 (2H, s), 2.76 (6H, s), 2.70 (4H, m), 1.76 (4H, m).

EXAMPLE 19

1-Methyl-6-(N-chloroacetylaminomethyl)-5-indanol

A solution of 850 mg of 1 methyl-5-indanol in 5 ml of a mixed solution of acetic acid and sulfuric acid (10:1 by volume) solution was mixed with 850 mg of N-hydroxymethyl chloroacetamide at room temperature under stirring for 2 hours. After reaction the reaction mixture was poured into 20 ml of water, extracted with ethyl acetate. The extract was washed with water, dried with anhydrous magnesium sulfate and concentrated under vacuum. The crude product thus obtained was purified by column chromatography on 100 g of Kiesel gel using an eluting agent comprising a mixture (20:1 by volume) of methylene chloride and ethyl acetate to provide 590 mg of the titled compound.

TLC (on a developing agent methylenechloride and ethylacetate in a volume ratio of 10:1): Rf=0.32.

IR (KBr tablet): $\nu = 3300, 2950, 2860, 1710, 1650, 1540, 1495, 1450, 1430, 1410, 1370, 1350, 1300, 1270, 1170, 1150, 1090, 1045, 1020, 925$ cm$^{-1}$.

NMR (CDCl$_3$): $\delta = 7.35$ (2H, broad, NH, OH), 6.82 (1H, s), 6.67 (1H, s), 4.35 (2H, d, J=6 Hz), 4.00 (2H, s), 3.30–2.60 (3H, m), 2.60–2.00 (1H, m), 2.00–1.20 (1H, m), 1.20 (3H, d, J=7 Hz).

EXAMPLE 20

1-Methyl-4-iodo-6-(N-chloroacetylaminomethyl)-5-indanol

A solution of 570 mg of 1-methyl-6-(N-chloroacetylaminomethyl)-5-indanol which was obtained in EXAMPLE 19 in 3 ml of acetic acid was mixed with 570 mg of monochloroiodine at room temperature followed by stirring at 100° C. for 2 hours. The resulting mixture was poured into 50 ml of water and extracted with ethyl acetate. The extract was washed with an aqueous solution of sodium thiosulfate (hypo) and then with water, dried with magnesium sulfate and condensed under vacuum. The residue was purified by column chromatography on silica gel using an eluting agent comprising a mixture (50:1) of methylene chloride and ethyl acetate to provide 410 mg of the titled compound.

Melting Point: 117°–120° C.

IR (KBr tablet): $\nu = 3300, 3150, 2950, 1630, 1545, 1440, 1430, 1405, 1365, 1330, 1290, 1275, 1245, 1225, 1200, 1165, 1150$ cm$^{-1}$.

NMR (CDCl$_3$): $\delta = 7.92$ (1H, —OH), 7.33 (1H, —NH—), 6.80 (1H, s), 4.37 (2H, d, J=6 Hz), 4.00 (2H, s), 3.50–3.00 (1H, m), 3.00–2.60 (2H, m), 2.60–2.00 (1H, m), 1.93–1.20 (1H, m), 1.20 (3H, d, J=7 Hz).

EXAMPLE 21

1-Methyl-4-iodo-6-aminomethyl-5-indanol hydrochloride

A solution of 380 mg of 1-methyl-4-iodo-6-(N-chloroacetylaminomethyl)-5-indanol which was obtained in EXAMPLE 20 in 4 ml of ethanol was mixed with 2 ml concentrated of hydrochloric acid and refluxed for 8 hours. The reaction mixture was concentrated to dryness under vacuum. The residue was washed with diethyl ether and dissolved in a small amount of methanol. The solution was mixed with diethyl ether to precipitate crystals which were then filtered and dried to provide 180 mg of the titled compound.

Melting Point: 168°–170° C. (decomposed).

TLC (on a developer of a mixture of n-butanol, acetic acid and water in a volume ratio of 5:3:2): Rf=0.76.

IR (KBr tablet): $\nu$=3400, 3200, 3020, 2950, 1605, 1495, 1450, 1430, 1380, 1335, 1300, 1275, 1240, 1150 cm$^{-1}$.

NMR (CD$_3$OD): $\delta$=7.00 (1H, s), 4.67 (4H, —OH, —NH$_3$), 2.80 (3H, m), 2.20 (1H, m), 1.55 (1H, m), 1.20 (3H, d, J=7 Hz).

EXAMPLE 22

1-Iodo-5,5-dimethyl-5,6,7,8-tetrahydro-2-naphthol

A solution of 3.97 g of 5,5-dimethyl-5,6,7,8-tetrahydro-2-naphthol in 12 ml of ethanol was mixed with 744 mg of ethylenediamine. To the resulting mixture was added dropwise an aqueous solution of 6.3 g of iodine and 5.3 g of potassium iodide in 8 ml of water in 1.5 hours. The reaction mixture was poured into 100 ml of water, extracted with diethyl ether. The extract was washed with water, dried with magnesium sulfate and concentrated under vacuum. The residue was purified by column chromatography on 400 g of silica gel using an eluting agent comprising a mixture of methylene chloride and cyclohexane (1:1 by volume) to provide 2.18 g of white crystals of the titled compound.

Melting Point: 65°–68° C.

TLC (on a developer of methylene chloride): Rf=0.70.

IR (KBr tablet method): $\nu$=3400, 3160, 2960, 2940, 2870, 1665, 1600, 1560, 1480, 1460, 1430, 1415, 1345, 1295, 1280, 1255, 935 cm$^{-1}$.

NMR (CDCl$_3$ solution): $\delta$=7.03 (1H, d), 6.69 (1H, d), 5.2-4.7 (1H, —OH), 2.77-2.50 (2H, m), 2.00-1.43 (4H, m), 1.23 (6H, s).

EXAMPLE 23

1-Iodo-3-(N-chloroacetylaminomethyl)-5,5-dimethyl-5,6,7,8-tetrahydro-2-naphthol

A solution of 2.08 g of 1-Iodo-5,5-dimethyl-5,6,7,8-tetrahydro-2-naphthol in 15 ml of a mixture of acetic acid and sulfuric acid (10:1 by volume) was mixed with 1.40 g of N-hydroxymethyl chloroacetamide at room temperature under stirring for 3 hours. Thereafter, the mixture was poured into water and extracted with ethyl acetate. Ethyl acetate was distilled off from the extract and the residue was purified by column chromatography on 200 g of silica gel using methylene chloride as an eluting agent to provide 1.89 g of white crystals of the titled compound.

Melting Point: 66°–70° C.

IR (KBr tablet method): $\nu$=3400, 3300, 2960, 2860, 1640, 1540, 1460, 1440, 1260, 1140, 1080 cm$^{-1}$.

NMR (CDCl$_3$ solution): $\delta$=7.53 (1H, s, —OH), 7.43-7.00 (1H, —NH—), 7.49 (1H, s), 4.17 (2H, d), 4.00 (2H, s), 2.77-2.50 (2H, m), 2.00-1.33 (4H, m), 1.23 (6H, s).

EXAMPLE 24

1-Iodo-3-aminomethyl-5,5-dimethyl-5,6,7,8-tetrahydro-2-naphthol Hydrochloride

A solution of 1.78 g of 1-Iodo-3-(N-chloroacetylaminomethyl)-5,5-dimethyl-5,6,7,8-tetrahydro-2-naphthol prepared in EXAMPLE 23 in 10 ml of ethanol was mixed with 3 ml of concentrated hydrochloric acid and heated at 100° C. for 4 hours followed by condensing under vacuum. To the residue was added diethyl ether to precipitate crystals which were filtered and recrystallized from a mixed solvent of ethanol and diethyl ether to provide 550 mg of white crystals of the title compound.

Melting Point: 120°–122° C.

TLC (on a developer of ethylacetate 3: acetic acid 1: water 1 (volume to volume ratio)):Rf=0.70.

IR (KBr tablet method): $\nu$=3380, 3040, 2960, 2870, 1610, 1470, 1415, 1300, 1220, 1145 cm$^{-1}$.

NMR (CD$_3$OD solution): $\delta$=7.23 (1H, s), 4.09 (2H, s), 2.83-2.49 (2H, m), 2.09-1.43 (4H, m), 1.27 (6H, s).

EXAMPLE 25

1-Iodo-3-aminomethyl-5,6,7,8-tetrahydro-2-naphthol Hydrobromide (1) Preparation of 3-Hydroxy-5,6,7,8-tetrahydro-2-naphthoic Acid Methyl Ester A 281 g sample of 3-hydroxy-5,6,7,8-tetrahydro-2-naphthoic acid was dissolved in 1.4 l of methanol, and while hydrogen chloride gas was supplied, the solution was first exposed to room temperature for 2 hours, and then heated at 60° to 70° C. for 4 hours. Methanol was distilled off under vacuum, water was added to the residue, which was then extracted with ethyl acetate. The ethyl acetate layer was washed with sodium bicarbonate until it became neutral, and then it was dehydrated and concentrated. The residual oily product was distilled under vacuum to provide 279 g of the title compound (1) having the following physical properties.

Boiling Point: 115°–116° C./0.07–0.08 mm Hg.

NMR (CDCl$_3$ solution): $\delta$=7.40 (1H, s), 6.57 (1H, s), 4.17 (3H, s), 2.87-2.17 (4H, m), 2.00-1.30 (4H, m).

(2) Preparation of 3-Hydroxy-5,6,7,8-tetrahydro-2-naphthoic Amide

To 300 ml of methanol saturated with ammonia gas at 0° C. was added 122 g of 3-hydroxy-5,6,7,8-tetrahydro-2-naphthoic acid methyl ester, and the mixture was maintained in an autoclave at 100° C. for 5 hours. After cooling, the precipitating solid was filtered off, washed with a small amount of methanol, and dried, giving 96 g of a pale yellow crystal having the following physical properties.

Melting Point: higher than 200° C.

IR (KBr tablet method): $\nu$=3240, 3190, 2940, 1660, 1640, 1585, 1500, 1425, 1365, 1270, 1100 cm$^{-1}$.

NMR (dimethylsulfoxide-d$_6$ solution): $\delta$=7.43 (1H, s), 6.48 (1H, s), 8.3-6.5 (broad —CONH$_2$, —OH), 2.85-2.18 (4H, m), 1.98-1.33 (4H, m).

(3) Preparation of 3-Aminomethyl-5,6,7,8-tetrahydro-2-naphthol Hydrochloride

To 2.5 l of dry tetrahydrofuran was first added 57 g of lithium aluminum hydride, then added gradually 82 g of the amide prepared in step (2), and the mixture was refluxed for 20 hours. After cooling, ethyl acetate was gradually added to the mixture to decompose excess lithium aluminum hydride. The reaction mixture was poured into 2 l of 2 N aqueous NaOH solution and extracted with ethyl acetate three times. The ethyl acetate layer was water washed, dehydrated, and concentrated under vacuum. Because partial acetylation of amino group occurred, the residue was dissolved in 1 l of ethanol and 150 ml of concentrated hydrochloric acid upon heating, and refluxed for 15 hours. After cooling, the precipitating solid was filtered off, and the mother liquor was concentrated to a small volume, followed by filtering off of the precipitating solid. A total of 50 g of the title compound (3) having the following physical properties was obtained.

Melting Point: 216°–218° C.

IR (KBr table method): $\nu = 3100, 2940, 2800-2300, 1560, 1510, 1440, 1200, 1120$ cm$^{-1}$.

NMR (dimethylsulfoxide-d$_6$): $\delta = 9.6$ (1H, broad), 8.1 (3H, broad), 7.87 (1H, s), 6.53 (1H, s), 4.1-3.5 (2H, m), 2.9-2.2 (4H, m), 2.0-1.4 (4H, m).

(4) Preparation of 3-Carbobenzyloxy-aminomethyl-5,6,7,8-tetrahydro-2-naphthol

In 450 ml of water was suspended 49.5 g of the amine hydrochloride obtained in step (3), and while cooling, 140 m of 2 N NaOH aqueous solution was added to the suspension. To the mixture was simultaneously added dropwise 135 ml of 2 N NaOH aqueous solution and 170 ml of 30% solution of carbobenzyloxychloride in toluene in about 30 minutes under stirring. After completion of dropwise addition, the reaction mixture was stirred for 30 minutes and extracted with ethyl acetate. The ethyl acetate layer was water washed, dehydrated and concentrated to a small volume. The precipitating solid was filtered off, which was then washed with cyclohexane containing about 5% ethyl acetate, and dried to provide 52 g of the title compound (4) having the following physical properties.

Melting Point: 113.5°–115° C.

IR (KBr tablet method): $\nu = 3300, 2940, 2850, 1670, 1555, 1505, 1295, 1100, 1000, 740$ cm$^{-1}$.

NMR (CDCl$_3$ solution): $\delta = 8.1$-7.63 (1H, —OH), 7.22 (5H, s), 6.70 (1H, s), 6.57 (1H, s), 5.67-5.25 (1H, —NH—CO—), 5.03 (2H, s), 4.17 (2H, d, J = 6 Hz), 2.93-2.35 (4H, m), 2.0-1.72 (4H, m).

(5) Preparation of 1-Iodo-3-carbobenzyloxy-aminomethyl-5,6,7,8-tetrahydro-2-naphthol In 750 ml of ethanol was dissolved 50 g of the compound (4) under heating, and 7.5 g (8.35 ml) of ethylenediamine was added to the solution. A mixture of 50.8 g of iodine and 41.5 g of potassium iodide was dissolved in 500 ml of water, and the resulting aqueous solution was added dropwise to the previously prepared solution over about 30 minutes under stirring at 30° C. After additional 1 hour's stirring, the precipitating solid was filtered off, which was washed with 50% ethanol, and dried to provide 59 g of the title compound (5) having the following physical properties.

Melting Point: 116°–117° C.

IR and NMR were exactly the same as those obtained for the compound of EXAMPLE 4.

(6) Preparation of 1-Iodo-3-aminomethyl-5,6,7,8-tetrahydro-2-naphthol Hydrobromide To 50 g of the compound (5) was added 120 ml of 30% solution of hydrogen bromide in acetic acid, and the mixture was maintained at room temperature for 30 minutes. After addition of 3 l of ether, the resulting mixture was left standing. The precipitating solid was filtered off, which was then washed with ether, and dried. A 28 g sample of the solid was dissolved in 100 ml of methanol, filtered on activated carbon, and the filtrate was combined with 200 ml of ether, after which the mixture was allowed to cool, and left standing. The precipitated solid was filtered off, washed with ether, and dried to obtain 19 g of the title compound (6) having the following physical properties.

Melting Point: 204°–206° C.

IR, NMR and TLC were exactly the same as those obtained for the compound of EXAMPLE 5.

While the invention has been described in detail and with reference to specific embodiments thereof, it will be apparent to one skilled in the art that various changes and modifications can be made therein without departing from the spirit and scope thereof.

What is claimed is:

1. A 2-aminomethyl phenol compound of the formula (I):

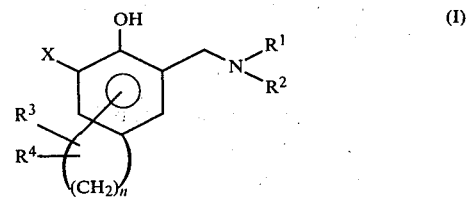

wherein X is a halogen atom; $R^1$, $R^2$, $R^3$ and $R^4$ which may be the same or different are each a hydrogen atom or a straight or branched chain alkyl group having 1 to 4 carbon atoms; and n is 2, 3, 4 or 5 or a pharmaceutically acceptable acid addition salt thereof.

2. The compound according to claim 1, wherein the 2-aminomethyl phenol derivative is 4-iodo-6-aminomethyl-5-indanol or a pharmaceutically acceptable acid addition salt thereof.

3. The compound according to claim 1, wherein the 2-aminomethyl phenol derivative is 4-aminomethyl-6-iodo-5-indanol or a pharmaceutically acceptable acid addition salt thereof.

4. The compound according to claim 1, wherein the 2-aminomethyl phenol derivative is 4-iodo-6-(N-methylaminomethyl)-5-indanol or a pharmaceutically acceptable acid addition salt thereof.

5. The compound according to claim 1, wherein the 2-aminomethyl phenol derivative is 4-iodo-6-(N,N-dimethylaminomethyl)-5-indanol or a pharmaceutically acceptable acid addition salt thereof.

6. The compound according to claim 1, wherein the 2-aminomethyl phenol derivative is 4-(N-methylaminomethyl)-6-iodo-5-indanol or a pharmaceutically acceptable acid addition salt thereof.

7. The compound according to claim 1, wherein the 2-aminomethyl phenol derivative is 4-(N,N-dimethylaminomethyl)-6-iodo-5-indanol or a pharmaceutically acceptable acid addition salt thereof.

8. The compound according to claim 1, wherein the 2-aminomethyl phenol derivative is 1-iodo-3-aminomethyl-5,6,7,8-tetrahydro-2-naphthol or a pharmaceutically acceptable acid addition salt thereof.

9. The compound according to claim 1, wherein the 2-aminomethyl phenol derivative is 1-aminomethyl-3- iodo-5,6,7,8-tetrahydro-2-naphthol or a pharmaceutically acceptable acid addition salt thereof.

10. The compound according to claim 1, wherein the 2-aminomethyl phenol derivative is 1-iodo-3-(N-methylaminomethyl)-5,6,7,8-tetrahydro-2-naphthol or a pharmaceutically acceptable acid addition salt thereof.

11. The compound according to claim 1, wherein the 2-aminomethyl phenol derivative is 1-iodo-3-(N,N-dimethylaminomethyl)-5,6,7,8-tetrahydro-2-naphthol or a pharmaceutically acceptable acid addition salt thereof.

12. The compound according to claim 1, wherein the 2-aminomethyl phenol derivative is 1-(N-methylaminomethyl)-3-iodo-5,6,7,8-tetrahydro-2-naphthol or a pharmaceutically acceptable acid addition salt thereof.

13. The compound according to claim 1, wherein the 2-aminomethyl phenol derivative is 1-(N,N-dimethylaminomethyl)-3-iodo-5,6,7,8-tetrahydro-2-naphthol or a pharmaceutically acceptable acid addition salt thereof.

14. The compound according to claim 1, wherein the 2-aminomethyl phenol derivative is 1-iodo-3-aminomethyl-5,5-dimethyl-5,6,7,8-tetrahydro-2-naphthol or a pharmaceutically acceptable acid addition salt thereof.

15. The compound according to claim 1, wherein the 2-aminomethyl phenol derivative is 1-methyl-4-iodo-6-aminomethyl-5-indanol or a pharmaceutically acceptable acid addition salt thereof.

* * * * *